United States Patent [19]

Jabr et al.

[11] Patent Number: 4,793,709

[45] Date of Patent: Dec. 27, 1988

[54] METHOD AND APPARATUS FOR MEASURING THE LOSSES OF AN OPTICAL CAVITY

[75] Inventors: Salim N. Jabr, Woodland Hills; Thomas M. Crawford, Thousand Oaks, both of Calif.

[73] Assignee: Litton Systems, Inc., Beverly Hills, Calif.

[21] Appl. No.: 766,483

[22] Filed: Aug. 16, 1985

[51] Int. Cl.$^4$ ............................................. G01N 21/55
[52] U.S. Cl. ..................................... 356/445; 356/124; 356/447
[58] Field of Search ............... 356/445, 124, 432, 447; 372/12, 25

[56] References Cited

U.S. PATENT DOCUMENTS 4,571,085  2/1986  Anderson ........................ 356/124 X

OTHER PUBLICATIONS

"Mirror Reflectometer Based on Optical Cavity Decay Time", Anderson et al., Applied Optics, Apr. 1984, pp. 1238–1245.

"Method For Measuring Reflection Coefficients Close To Unity", Vinokurov et al., Novosibirsk, 1979.

Primary Examiner—Vincent P. McGraw
Assistant Examiner—S. A. Turner
Attorney, Agent, or Firm—Elliott N. Kramsky

[57] ABSTRACT

A method and associated apparatus for measuring the intensity decay time of an optical cavity is particularly useful for accurate measurement of cavities of the type that include highly reflective mirrors. In the method, apparatus is provided for generating at least one pulse of laser light having a bandwidth that exceeds the resonant frequency spacing of the optical cavity and for directing that pulse into the cavity. The intensity of the light within the cavity is then measured and the amount of time is determined for such intensity to decay from a first predetermined value to a second predetermined value.

13 Claims, 2 Drawing Sheets

METHOD AND APPARATUS FOR MEASURING THE LOSSES OF AN OPTICAL CAVITY

BACKGROUND

1. Field of the Invention

The present invention relates to a method and apparatus for measuring the intensity decay time of an optical cavity at various wavelengths. More particularly, this invention pertains to such a method and apparatus of particular utility with regard to cavities of the type that include low loss mirrors.

2. Description of the Prior Art

Numerous optical instruments are critically dependent upon mirror parameters. For example, in a ring laser gyroscope, mirrors located at the intersections of three or four cavities internal to a glass ceramic block successively reflect counter-rotating beams of laser light that, upon transmission through a partially-transmissive mirror, are analyzed for frequency content. It is essential that the operating parameters of the mirrors of such an instrument be well-known to permit accurate evaluation of the optical output of this device. Numerous other applications require detailed knowledge of the system mirrors. Further, one may design improved optical systems when detailed a priori knowledge of the mirror characteristics, and the thin films for forming mirror surfaces, is available.

The mirrors generally employed in high accuracy laser instrumentation commonly comprise a substrate having an optical coating thereon. This coating may be applied in a plurality of layers. For example, in the fabrication of mirrors for current state-of-the art ring laser gyroscopes, a number of thin film coating layers, each having a thickness of about 1000 Angstroms or one-quarter wavelength, are applied to a glass ceramic substrate. The number of layers applied may vary from 10 to 50, with most coatings comprising about 21 or 22 layers.

While the mirrors can play a crucial role in the performance of such optical instruments, coating characteristics may vary considerably from manufacturer to manufacturer, even in the presence of identical specifications. Thus, it is highly desirable to have and utilize a device for measuring the actual characteristics of the mirror and the constituent thin films.

A theoretical framework for measuring the loss of highly reflecting mirror coatings and transmission of low-loss antireflection coatings is disclosed by Dana Z. Anderson, Josef C. Frisch and Carl S. Masser in "Mirror Reflectometer Based on Optical Decay Time", *Applied Optics.*, Vol. 23, No. 8 (Apr. 15, 1984). The artical establishes that total mirror loss (the sum of scattering, transmission and absorption losses) may be found by analysis of its operation within an optical cavity. (An optical cavity may be defined as an enclosed cavity wherein light is directed between at least two mirrors.) The total mirror loss may then be established from the cavity intensity decay time c, the optical path length, L, of the cavity and the speed of light c. Once the decay time cavity number is known, other important mirror parameters, including finesse, reflectivity and reflectivity product may be easily derived.

The measurement of cavity lengths is relatively trivial and the speed of light a known value. The above-mentioned article proposes a method for determining the cavity time constant by brief laser energization of the cavity followed by timing of the decay in the intensity of the light within the cavity (measured as transmitted through a partially-transmissive cavity mirror). A very narrow bandwidth laser is used to generate the energy for exciting cavity resonance. This laser is always "on" and a short burst of light therefrom is shuttered through crossed polarizers by means of a Pockels cell. The narrow-band laser is allowed to drift in frequency, occasionally and randomly drifting to a resonant frequency of the cavity. (The article suggests that sweeping or frequency control of the narrow laser are thereby avoided.) The cavity is energized so that a measurable amount of light will be detected by the system electronics as the laser drifts to a cavity resonant frequency. When this occurs, a photodetector detects the light intensity within the cavity, the laser is shuttered, and the decay time of the cavity measured.

While the method is theoretically sound, the apparatus as disclosed above is flawed in a number of respects of particular significance with regard to the accuracy required in the measurement of low-loss mirrors. A high reflectively or low-loss mirror is one which loses or transmits less than 200 parts per million of incident illumination. The optical shutter of the "on" laser admits an irreducible and difficult-to-ascertain amount of "baseline" illumination at all times, "on" or "off". This illumination prevents the user from knowing the precise intensity values for the start and stop points between which the cavity decay time is counted. Since only very low levels of illumination are transmitted by low-loss mirrors, such background effects are particularly harmful when measuring highly reflective mirrors. Additionally, by allowing the laser to drift into and out of the resonant frequency of the cavity, false readings can occur that result from the sometime nonmonotonic nature of the intensity decay curve for a cavity energized by a laser that may rapidly drift into and out of cavity resonance, causing re-excitation of the cavity to occur after the initiation of the "exponential" decay timing has been signalled to the electronic timing subsystem of the test apparatus.

SUMMARY OF THE INVENTION

The foregoing and additional shortcomings of the prior art are addressed and overcome by the present invention that provides, in a first aspect, apparatus for measuring the intensity decay time of an optical cavity. Such apprtus includes a pump laser for generating at least one pulse of optical energy. Means, responsive to the pump laser, are provided for producing optical energy at a preselected wavelength with a bandwidth that exceeds the resonant frequency spacing of the optical cavity. Means are additionally provided for coupling this optical energy into the cavity. The apparatus includes means for measuring the intensity of the optical energy within the cavity and for measuring the amount of time for that intensity to decay from a first predetermined value to a second predetermined value.

In a second aspect, the present invention provides a method for measuring the intensity decay time of an optical cavity. This method includes the step of generating at least one pulse of laser light at a preselected wavelength having a bandwidth that exceeds the resonant frequency spacing of the cavity at such wavelength. This laser light is directed into the cavity and its intensity within the cavity measured. Finally, the amount of time for this intensity to decay from a first predetermined value to a second predetermined value is measured.

The foregoing and additional advantages and features of the present invention will become apparent from the detailed description of the invention that follows. This description is accompanied by a set of drawing figures. Numerals point out the various features of the invention in the figures and in the detailed description, like numerals referring to like features throughout.

DETAILED DESCRIPTION

Figure 1:
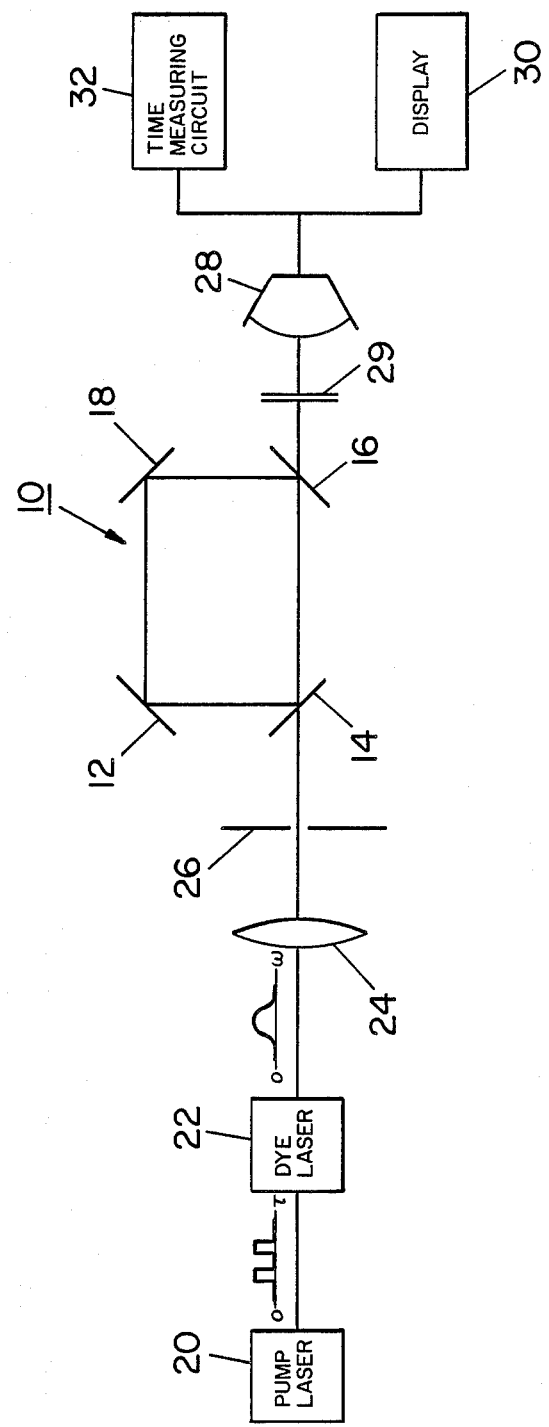
FIG. 1 is a schematic view of the measuring apparatus of the invention.

Turning now to the drawings, FIG. 1 is a schematic view of the mirror measurement apparatus of the invention. The apparatus is arranged for measuring the intensity decay time $\tau_c$ of an optical cavity 10 which includes a plurality of mirrors 10, 12, 14 and 16 for directing an input beam of light about the cavity 10. While the cavity may have a number of geometries, the mirrors 12, 14, 16 and 18 are preferentially arranged so that the input mirror 14 and the output mirror 16 comprise the two highest transmitting mirrors of the set in the event all mirrors are not nominally identical in this regard.

Laser light is directed at the cavity, entering it through the input mirror 14. Within the cavity 10, this light is directed about the optical path defined therein by the mirrors 12, 14, 16 and 18. An indication of the intensity of the light within the cavity is obtained by examination of the portion of this light transmitted through the output mirror 16. The relatively high reflectivities of the mirrors of the cavity 10 permit the input and output of relatively small amounts of light. Thus, this factor, in addition to the great accuracies of measurement required with regard to the precision mirrors of the cavity 10, the input of difficult-to-ascertain amounts of background illumination may do great harm to the usefulness of the mirror measurements obtained.

In the invention, laser light capable of attaining a transition from a fully off or "black" mode to a fully illuminated on mode is generated which eliminates the background problem of the prior art. A laser 20, such as a nitrogen or Nd:YAG laser generates pulses of laser energy of five to ten nanosecond duration. Such pulses, separated by periods of no energy transmission, are directed at and serve to pump a tuneable dye laser 22.

The tuneable dye laser 22 is excited by the pumping pulses of the laesr 20 to emit laser light having a preselected frequency bandwidth. The laser 22 is known in the art to include a chemical dye amplifying medium, such as Rhodamine perchlorate or Rhodamine tetrafluoraborate whereby, when pumped by laser energy a preselected frequency bandwidth of laser energy is excited. The wavelength of the laser light transmitted by the laser 22 in response to the pumping is tuneable by selective rotation of a grating therein to permit study of cavity mirrors at a number of further defined frequencies within the bandwidth of the chosen dye. (Representative dye bandwidths cover a range of laser wavelengths of about 200 Angstroms.) The bandwidth of the light emitted from the laser 22 is selected so that a plurality of resonances of the cavity 10 are included within its scope. That is, the bandwidth of the light excited is adequate to excite the cavity to resonance as it exceeds the resonant frequency separation (also known as the "free specral range") of the cavity 10 for the wavelength of the light being studied therein.

The laser light output is polarized by conventional means associated with the pump laser 20 and/or the tuneable dye laser 22. The type of polarization will vary in accordance with the geometry of the cavity 10 that, in turn, is reflected in the type of mirror coating employed. The selection and adjustment of polarization in accordance with the foregoing criteria is well-known in the art.

A mode-matching lens 24 accepts the light output of the laser 22. The lens 24 is designed for coupling the fundamental modes of the laser 22 to those of the cavity 10. An aperture 26 is preferentially included between the mode-matching lens 24 and the input mirror 14 to mask off-axis modes that may introduce different decay times into the cavity 10. The design of such mode-matching optics 24 is well-understood in the art of spatial filtering.

Some amount of the light within the cavity 10, as excited by the input of the laser light energy generated and conditioned as described above, is transmitted through the output mirror 16. The intensity of this light is transformed into an electrical signal upon receipt by a photoelectronic means 28. In accordance with the range of cavity intensity decay times investigated by the apparatus of the invention, the photoelectronic means 28 has a relatively fast response time, preferably shorter than ten nanoseconds. Both photomultipliers and photodiodes are presently commerically available with such capabilities. The photoelectronic means 28 is protected from harmful saturation by an attenutator 29 positioned between it and the output mirror 16.

The signal produced by the photoelectric means 28 may be applied to both a display means 30, such as a conventional oscilloscope, and to a time-measuring circuit 32. The display means 30 provides the user with a visual display of the voltage buildup and decline of the signal from the photoelectronic means 28 that mirrors the buildup and decay of the intensity of light within the cavity upon transmission of a pulse of laser light as generated by the pumped dye laser 22.

The time-measuring circuit 32 detects a first and a second (lower) preselected voltage level of the output of the photoelectric means and times the duration of time required for the signal to decline therebetween. The circuit 32 may comprise a pulse digitizer such as the commerically available model 7D20 of the Tektronix Corporation of Beaverton, Oreg. Such apparatus includes an associated plotter. Alternatively, it may comprise a circuit of the type known as a boxcar averager commercially available from Princeton Applied Research of Princeton, N.J. In the latter event, a plotter may be associated therewith for providing a least squares display of the decay of the level of the electrical signal. Further, when a boxcar averager is employed, a conductor must be provided between the pump laser 12 and the averager for triggering the averager upon generation of the optical pulse.

Figure 2:
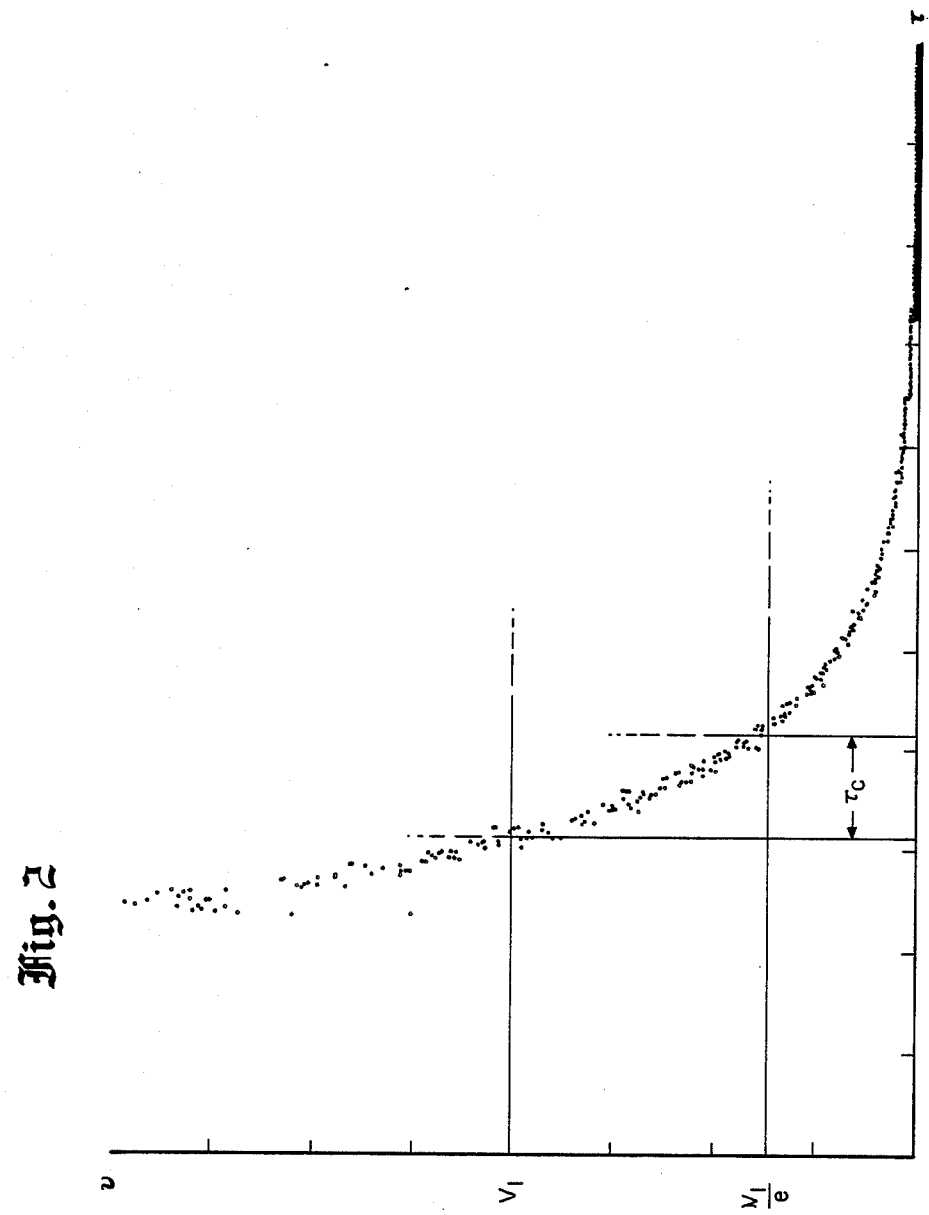
FIG. 2 is a graphical representation of data derived in accordance with the apparatus of the invention.

FIG. 2 is a graphical representation of data generated in accordance with the method and apparatus of the invention. The data is a plot of Tektronix model 7D20 pulse digitizer measurements of the voltage signal output of a photoelectronic means 28 arranged in accordance with the invention. The cavity 10, unlike the ring-like cavity of FIG. 1, was a linear, two-mirror cavity having a length of 10 centimeters. A Rhodamine 640 dye was employed in association with the tuneable dye laser 22. The bandwidth of the output of the laser 22 was .1 wave number.

Time is plotted on the abscissa of the graph in gradations of 500 nanoseconds per division. Voltage values are plotted on the ordinate of the graph.

As can be seen, two horizontal lines, corresponding to voltage values $V_1$ and $V_1/e$ are indicated. The first value represents an artibrarily chosen value within the predetermined range of signal outputs of the photoelectronic means 28 while the latter value in simply the first value divided by e, the base of the natural logarithmic scale. Assuming an exponential function, it is well-known that the time required for such function to traverse between these two values is the time constant, $\tau$, of the exponential decay function. In the case of the physical relevance of the data as plotted on the graph of FIG. 2, this time constant represents the intensity decay time, $\tau_c$, of the cavity 10.

The data as plotted in FIG. 2 indicates that, prior to the application of the pulse of laser energy, no output of the photoelectronic means 28 is generated, indicating no background illumination. Thereafter, a very rapid rise in this output, corresponding to the excitation of the cavity 10, occurs. This is followed by a clearly exponential decay of the optical energy of the cavity, as predicted by theory. The timing apparatus of the pulse digitizer is triggered between the indicated voltage levels of the signal output of the optoelectronic means 28 to yield a cavity intensity decay time of 522.46 nanoseconds.

Insofar as the mirror under study, the data as presented in the plot of FIG. 2 discloses a rather high total mirror loss of 1335 parts per million. This may be adequate or inadequate for the use intended and the wavelength studied. Subsequent studies at other wavelengths may be made by adjusting or tuning the laser 22 with other dyes. Thus, the potential of the apparatus of the invention as a design tool is evident.

Since all configurations of the cavity 10 require at least two mirrors, some analysis must be done to determine the loss of a single mirror. Well-known methods, including the use of a reference mirror of known loss value, and the making of successive measurement among a group of mirrors with systematic mirror substitutions, may be employed to associate a loss value with a particular mirror.

In addition to the measurement of mirror loss, the method and apparatus of this invention is readily adapted to the measurement of losses of antireflection coatings. Some obvious modification of the apparatus; namely, the insertion of the coating, as an intracavity element mounted on a substrate, is required.

Thus is it seen that there has been brought to the art a new and improved method and apparatus for measuring the intensity decay time of an optical cavity. By utilizing the teachings of the invention, one may measure significant mirror and anti-reflection coating parameters with great accuracy and simplicity.

While this invention has been described with reference to a presently preferred emboidment, its scope is limited only insofar as defined in the following set of claims and all equivalents thereof.

What is claimed is:

1. Apparatus for measuring the intensity decay time of an optical cavity comprising, in combination:
    (a) a pump laser;
    (b) means responsive to said pump laser for producing a pulse of optical energy having a bandwidth that exceeds the resonant mode spacing of said cavity whereby multiple resonant modes of said cavity are simultaneously excited by said pulse;
    (c) means for injecting said pulse of optical energy into said cavity;
    (d) means for measuring the intensity of said injected optical energy within said cavity; and
    (e) means for measuring the amount of time for said intensity to decay from a first predetermined value to a second predetermined value.

2. Apparatus as defined in claim 1 further characterized in that said means for producing optical energy having a bandwidth that exceeds the resonant frequency spacing of said cavity is a tuneable dye laser.

3. Apparatus as defined in claim 2 further characterized in that at least one pulse of optical energy is between five and ten nanoseconds.

4. Apparatus as defined in claim 3 wherein said pump laser is a nitrogen laser.

5. Apparatus as defined in claim 3 wherein said pump laser is a Nd:YAG laser.

6. Apparatus as defined in claim 2 further including means for displaying the intensity of said optical energy.

7. Apparatus as defined in claim 6 wherein said means for measuring the intensity of said optical energy further includes:
    (a) means for producing an electrical signal responsive to said intensity; and
    (b) means for making a plurality of measurements of said signal.

8. Apparatus as defined in claim 7 wherein said means for producing an electrical signal is characterized by a response time of less than ten nanoseconds.

9. Apparatus as defined in claim 8 wherein said means for producing an electrical signal is a photodiode.

10. Apparatus as defined in claim 8 wherein said means for producing an electrical signal is a photomultiplier.

11. A method for measuring the intensity decay time of an optical cavity comprising the steps of:
    (a) generating a pulse of laser light at a preselected wavelength having a bandwidth that exceeds the resonant mode spacing of said cavity; and
    (b) injecting said pulse into said cavity whereby multiple resonant modes of said cavity are simultaneously excited; then
    (c) measuring the intensity of laser light within said cavity; and
    (d) measuring the amount of time for said intensity to decay from a first predetermined level to a second predetermined level.

12. A method as defined in claim 11 wherein said second predetermined value is 1/e times said first determined value.

13. A method of measuring losses in an optical cavity, comprising the steps of:
    (a) coupling a laser pulse into the cavity, the laser pulse having a plurality of longitudinal modes and exciting, in the cavity, multiple resonant modes; and
    (b) determining the time dependence of the decay of the laser pulse in the cavity.

* * * * *